(12) United States Patent
Litvak

(10) Patent No.: US 8,391,988 B2
(45) Date of Patent: Mar. 5, 2013

(54) METHODS AND SYSTEMS FOR PRESENTING AN AUDIO SIGNAL TO A COCHLEAR IMPLANT PATIENT

(75) Inventor: Leonid M. Litvak, Los Angeles, CA (US)

(73) Assignee: Advanced Bionics, Valencia, CA (US)

( * ) Notice: Subject to any disclaimer, the term of this patent is extended or adjusted under 35 U.S.C. 154(b) by 201 days.

(21) Appl. No.: 13/004,627

(22) Filed: Jan. 11, 2011

(65) Prior Publication Data

US 2011/0106211 A1    May 5, 2011

Related U.S. Application Data

(62) Division of application No. 11/858,649, filed on Sep. 20, 2007, now Pat. No. 7,904,165.

(60) Provisional application No. 60/846,296, filed on Sep. 21, 2006.

(51) Int. Cl.
 *A61N 1/36* (2006.01)
 *A61F 11/04* (2006.01)
 *H04R 25/00* (2006.01)

(52) U.S. Cl. ........................................................ 607/55

(58) Field of Classification Search .............. 607/55–57, 607/137
See application file for complete search history.

(56) References Cited

U.S. PATENT DOCUMENTS

| | | | |
|---|---|---|---|
| 4,819,647 | A | 4/1989 | Byers et al. |
| 6,129,753 | A | 10/2000 | Kuzma |
| 6,219,580 | B1 | 4/2001 | Faltys et al. |
| 6,272,382 | B1 | 8/2001 | Faltys et al. |
| 6,308,101 | B1 | 10/2001 | Faltys et al. |
| 2004/0252850 | A1 | 12/2004 | Turicchia et al. |

OTHER PUBLICATIONS

International Search Report and Written Opinion received in International Application No. PCT/US07/79156 dated Aug. 1, 2008.
Non-Final Office Action received for U.S. Appl. No. 11/858,649 dated May 4, 2010.

*Primary Examiner* — Brian T Gedeon

(74) *Attorney, Agent, or Firm* — AdvantEdge Law Group, LLC

(57) ABSTRACT

An exemplary signal processing unit includes a plurality of filters configured to divide an audio signal into a plurality of analysis channels, one or more detection stages configured to detect an energy level within each of said analysis channels, a selection stage configured to select one or more of said analysis channels for presentation to a patient, a synthesizer stage configured to synthesize said selected analysis channels, and a mapping stage configured to map said selected analysis channels to a number of stimulation channels within an implantable cochlear stimulator, wherein a total number of said analysis channels is greater than a total number of said stimulation channels.

11 Claims, 8 Drawing Sheets

METHODS AND SYSTEMS FOR PRESENTING AN AUDIO SIGNAL TO A COCHLEAR IMPLANT PATIENT

RELATED APPLICATIONS

The present application is a divisional application of U.S. patent application Ser. No. 11/858,649, filed Sep. 20, 2007, entitled "Methods and Systems for Presenting an Audio Signal to a Cochlear Implant Patient," and issued as U.S. Pat. No. 7,904,165, which claims priority under 35 U.S.C. §119(e) to U.S. Provisional Patent Application No. 60/846,296, filed Sep. 21, 2006, and entitled "Methods and Systems for Presenting an Audio Signal to a Cochlear Implant Patient." Both of these applications are incorporated herein by reference in their respective entireties.

BACKGROUND INFORMATION

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that acoustic signals reach the cochlea and the hair cells. Some types of conductive hearing loss may also be treated by surgical procedures.

Sensorineural hearing loss, on the other hand, is due to the absence or the destruction of the hair cells in the cochlea which are needed to transduce acoustic signals into auditory nerve impulses. Thus, people who suffer from sensorineural hearing loss are unable to derive any benefit from conventional hearing aid systems.

To overcome sensorineural hearing loss, numerous cochlear implant systems—or cochlear prosthesis—have been developed. Cochlear implant systems bypass the hair cells in the cochlea by presenting electrical stimulation directly to the auditory nerve fibers. Direct stimulation of the auditory nerve fibers leads to the perception of sound in the brain and at least partial restoration of hearing function. To facilitate direct stimulation of the auditory nerve fibers, an array of electrodes may be implanted in the cochlea. The electrodes form a number of stimulation channels through which electrical stimulation pulses may be applied directly to auditory nerves within the cochlea.

Hence, an audio signal may be presented to a patient by processing and translating the audio signal into a number of electrical stimulation pulses. The stimulation pulses may then be applied directly to auditory nerves within the cochlea via one or more of the stimulation channels.

Typical cochlear implant systems also include an audio signal processor. The signal processor is configured to process an audio signal by dividing the audio signal into a number of frequency ranges or analysis channels with a number of band-pass filters. In typical cochlear implant systems, the total number of analysis channels is equal to the total number of stimulation channels.

However, it is often undesirable to present the signals contained within all of the analysis channels to a patient at the same time. For example, if an incoming audio signal contains human speech in the presence of a lot of background noise, the patient may not be able to distinguish the human speech from the background noise if all of the analysis channels are presented to the patient simultaneously.

SUMMARY

Methods of presenting an audio signal to a cochlear implant patient include dividing the audio signal into a plurality of analysis channels, detecting an energy level within each of the analysis channels, selecting one or more of the analysis channels for presentation to the patient, synthesizing the selected analysis channels, and mapping the synthesized analysis channels to one or more stimulation channels.

Systems for presenting an audio signal to a cochlear implant patient include a signal processor and an implantable cochlear stimulator communicatively coupled to the signal processor. The signal processor is configured to divide the audio signal into a plurality of analysis channels, detect an energy level within each of the analysis channels, select one or more of the analysis channels for presentation to the patient, and synthesize the selected analysis channels. The implantable cochlear stimulator is configured to apply a stimulation current during a stimulation frame to a cochlea of the patient via one or more stimulation channels in accordance with information contained within the synthesized channels.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Methods and systems for presenting an audio signal to a cochlear implant patient are described herein. A signal processor is configured to divide the audio signal into a plurality of relatively narrow analysis channels, detect an energy level within each of the analysis channels, select one or more of the analysis channels for presentation to the patient, and synthesize the selected analysis channels. An implantable cochlear stimulator may then apply a stimulation current representative of the audio signal during a stimulation frame to a cochlea of the patient via one or more broader stimulation channels in accordance with information contained within the synthesized channels. In some examples, the total number of analysis channels is greater than the total number of stimulation channels. In this manner, the likelihood that relevant information within an audio signal will be detected and presented to a patient is increased.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
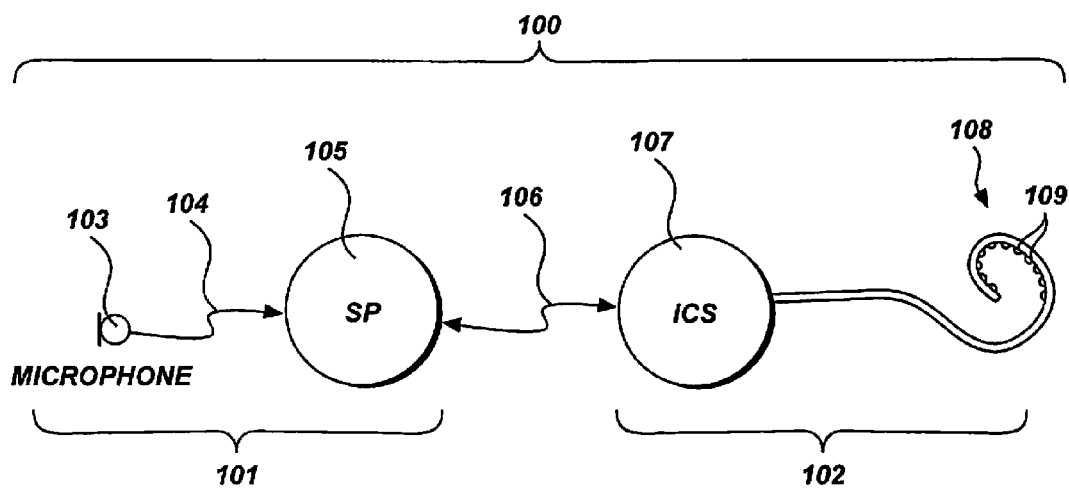
FIG. 1 illustrates an exemplary cochlear implant system according to principles described herein.

FIG. 1 illustrates an exemplary cochlear implant system 100 that may be used in accordance with the present methods and systems. Exemplary cochlear implant systems suitable for use as described herein include, but are not limited to, those disclosed in U.S. Pat. Nos. 6,219,580; 6,272,382; and 6,308,101, all of which are incorporated herein by reference in their respective entireties. The cochlear implant system 100 of FIG. 1 includes a signal processor portion 101 and a cochlear stimulation portion 102. The signal processor portion 101 may include a signal processor (SP) 105, a microphone 103, and/or additional circuitry as best serves a particular application. The cochlear stimulation portion 102 may include an implantable cochlear stimulator (ICS) 107, a number of electrodes 109 disposed on a lead 108, and/or additional circuitry as best serves a particular application. The components within the signal processor portion 101 and the cochlear stimulation portion 102 will be described in more detail below.

The microphone 103 of FIG. 1 is configured to sense acoustic signals and convert the sensed signals to corresponding electrical signals. The electrical signals are sent from the microphone 103 to the SP 105 via a communication link 104. Alternatively, the microphone 103 may be connected directly to, or integrated with, the SP 105. The SP 105 processes these converted acoustic signals in accordance with a selected signal processing strategy to generate appropriate control signals for controlling the ICS 107. These control signals may specify or define the polarity, magnitude, location (i.e., which electrode pair or electrode group receive the stimulation current), and timing (i.e., when the stimulation current is to be applied to a particular electrode pair) of the stimulation current that is generated by the ICS 107.

The lead 108 shown in FIG. 1 is configured to be inserted within a duct of the cochlea. As shown in FIG. 1, the lead 108 includes a multiplicity of electrodes 109, e.g., sixteen electrodes, spaced along its length. It will be understood, however, that any number of electrodes 109 may be disposed on the lead 108. The lead 108 may be substantially as shown and described in U.S. Pat. No. 4,819,647 or 6,129,753, each of which is incorporated herein by reference in its respective entirety. As will be described in more detail below, electronic circuitry within the ICS 107 is configured to generate and apply stimulation current to the cochlea via selected stimulation channels (i.e., pairs or groups of the individual electrodes 109) in accordance with a specified stimulation pattern defined by the SP 105.

The ICS 107 and the SP 105 may be electronically connected via a suitable data or communication link 106. It will be understood that the data communication link 106 may include a bi-directional communication link and/or one or more dedicated uni-directional communication links.

In some examples, the SP 105 and the microphone 103 comprise an external portion of the cochlear implant system 100 and the ICS 107 and the electrode lead 108 comprise an implantable portion of the system 100 that is implanted within a patient's body. In alternative embodiments, one or more portions of the SP 105 are included within the implantable portion of the cochlear implant system 100.

The external and implantable portions of the cochlear implant system 100 may each include one or more coils configured to transmit and receive power and/or control signals via the communication link 106. For example, the external portion of the cochlear implant system 100 may include an external coil (not shown) and the implantable portion of the cochlear implant system 100 may include an implantable coil (not shown). The external coil and the implantable coil may be inductively coupled to each other, thereby allowing data to be transmitted therebetween. The data may include, for example, the magnitude and polarity of a sensed acoustic signal. The external coil may also transmit power from the external portion to the implantable portion of the cochlear implant system 100. It will be noted that, in some embodiments, both the SP 105 and the ICS 107 may be implanted within the patient, either in the same housing or in separate housings. If the SP 105 and the ICS 107 are in the same housing, the communication link 106 may be realized with a direct wire connection within such housing. If the SP 105 and the ICS 107 are in separate housings, the communication link 106 may include one or more inductive links, for example.

Figure 2:
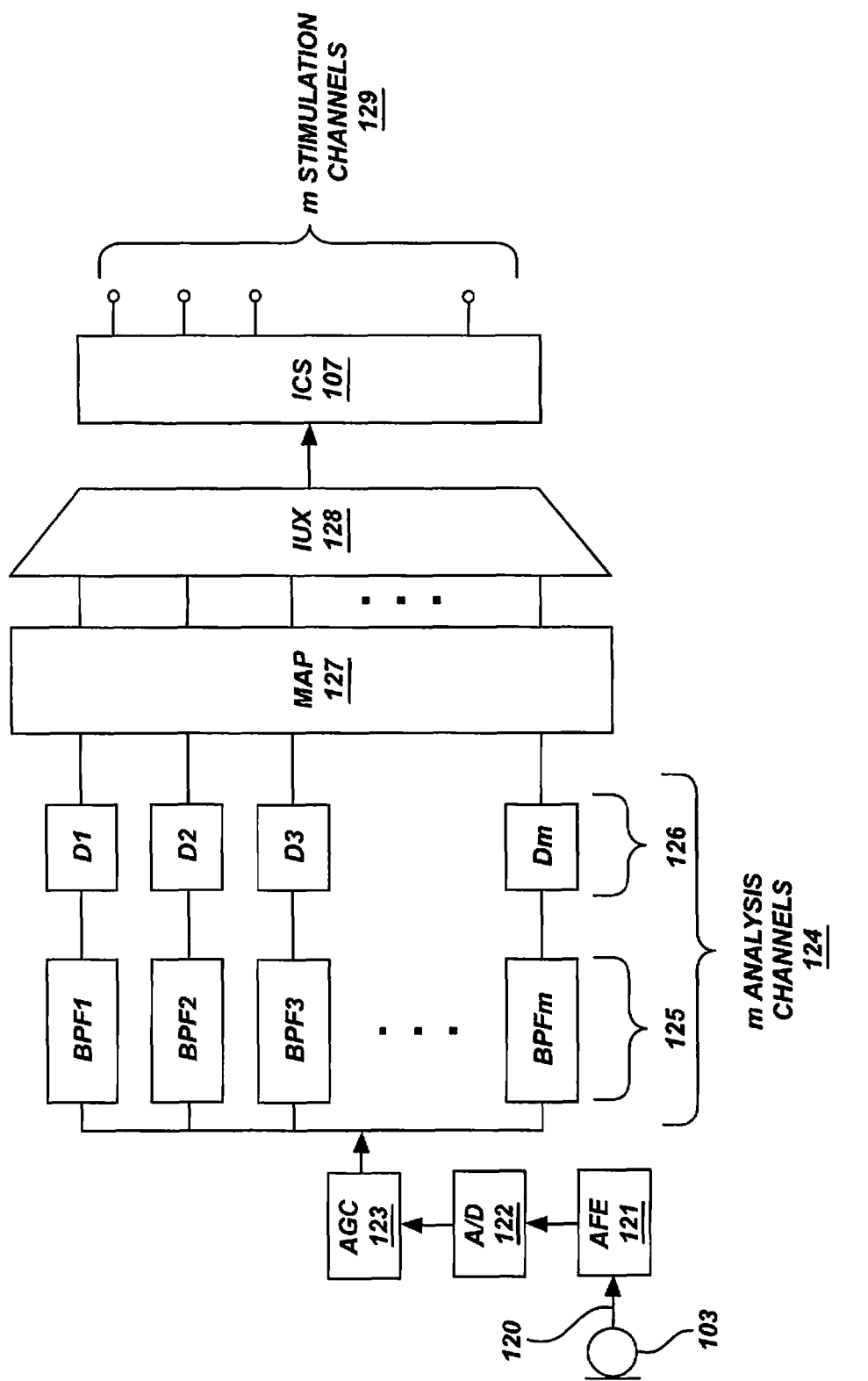
FIG. 2 is a functional block diagram of an exemplary signal processor and implantable cochlear stimulator according to principles described herein.

FIG. 2 is a functional block diagram of an exemplary SP 105 and ICS 107. The functions shown in FIG. 2 are merely representative of the many different functions that may be performed by the SP 105 and/or the ICS 107. A more complete description of the functional block diagram of the SP 105 and the ICS 107 is found in U.S. Pat. No. 6,219,580, which is incorporated herein by reference in its entirety.

As shown in FIG. 2, the microphone 103 senses acoustic information, such as speech and music, and converts the acoustic information into one or more electrical signals. These signals are then amplified in audio front-end (AFE) circuitry 121. The amplified audio signal is then converted to a digital signal by an analog-to-digital (A/D) converter 122. The resulting digital signal is then subjected to automatic gain control using a suitable automatic gain control (AGC) function 123.

After appropriate automatic gain control, the digital signal is then processed in one of a number of digital signal processing or analysis channels 124. For example, the SP 105 may include, but is not limited to, eight analysis channels 124. Each analysis channel 124 may respond to a different frequency content of the sensed acoustical signal. In other words, each analysis channel 124 includes a band-pass filter (BPF1-BPFm) 125 or other type of filter such that the digital signal is divided into m analysis channels 124. The lowest frequency filter may be a low-pass filter, and the highest frequency filter may be a high-pass filter.

As shown in FIG. 2, each of the m analysis channels 124 may also include an energy detection stage (D1-Dm) 126. Each energy detection stage 126 may include any combination of circuitry configured to detect the amount of energy contained within each of the m analysis channels 124. For example, each energy detection stage 126 may include a rectification circuit followed by an integrator circuit. As will be described in more detail below, the cochlear implant system 100 may be configured to determine which of the m analysis channels 124 are presented to the patient via the stimulation channels 129 by analyzing the amount of energy contained in each of the m analysis channels 124.

After energy detection, the signals within each of the m analysis channels 124 are forwarded to a mapping stage 127. The mapping stage 127 is configured to map the signals in each of the m analysis channels 124 to one or more of M stimulation channels 129. In other words, the information contained in the m analysis channels 124 is used to define the stimulation current pulses that are applied to the patient by the ICS 107 via the M stimulation channels 129. As mentioned previously, pairs or groups of individual electrodes 109 make up the M stimulation channels.

In some examples, the mapped signals are serialized by a multiplexer 128 and transmitted to the ICS 107. The ICS 107 may then apply stimulation current via one or more of the M stimulation channels 129 to one or more stimulation sites within the patient's cochlea. As used herein and in the appended claims, the term "stimulation site" will be used to refer to a target area or location at which the stimulation current is applied. For example, a stimulation site may refer to a particular location within the neural tissue of the cochlea. Through appropriate weighting and sharing of currents between the electrodes 109, stimulation current may be applied to any stimulation site along the length of the lead 108.

Figure 3:
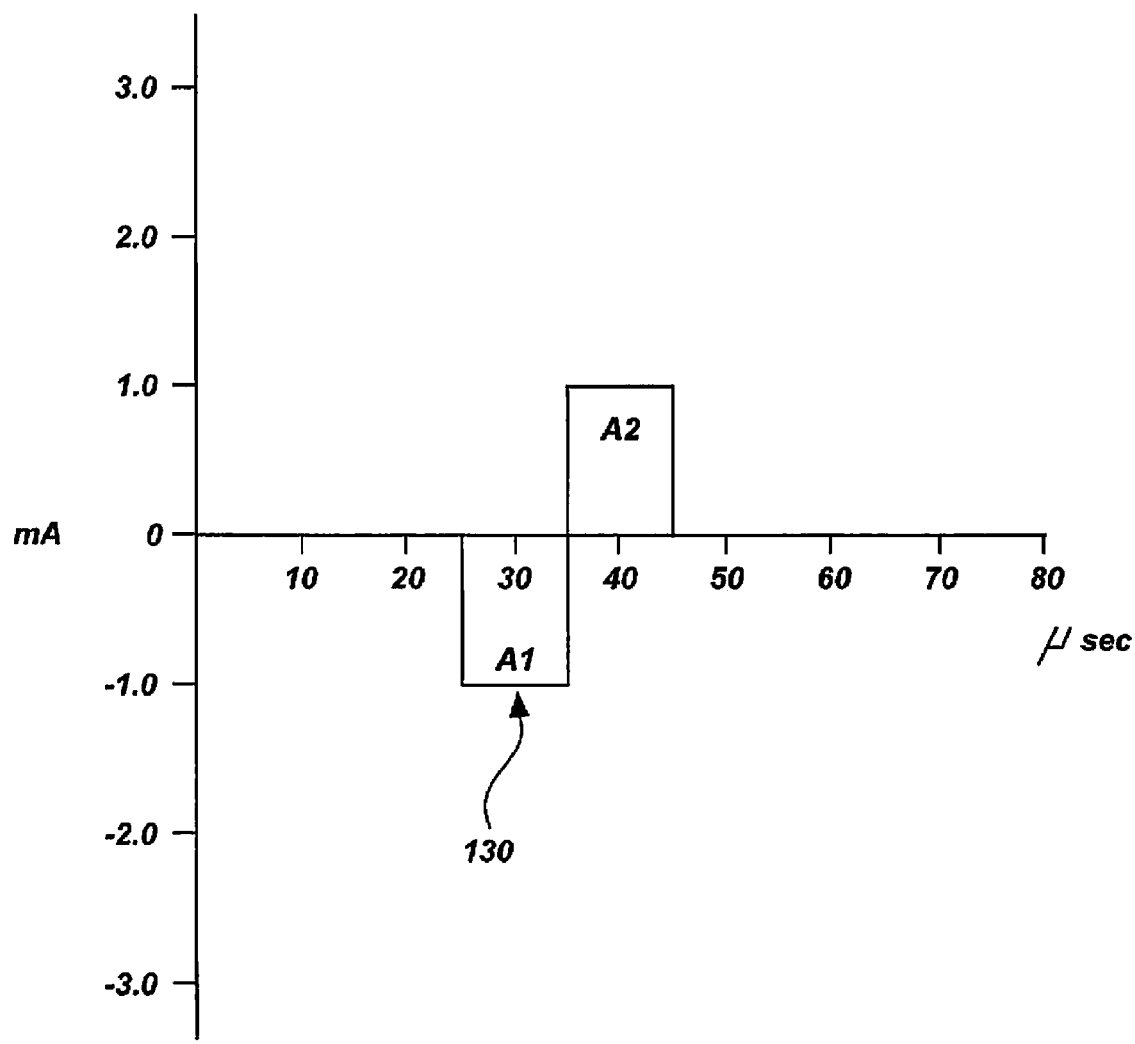
FIG. 3 illustrates an exemplary stimulation current pulse that may be delivered to neural tissue via one or more stimulation channels according to principles described herein.

FIG. 3 illustrates an exemplary stimulation current pulse 130 that may be delivered to neural tissue via one or more of the stimulation channels 129. The stimulation current pulse 130 of FIG. 3 is biphasic. In other words, the pulse 130 includes two parts—a negative first phase having an area A1 and a positive second phase having an area A2. In some implementations, the negative phase A1 causes neural tissue to depolarize or fire. The biphasic stimulation pulse 130 shown in FIG. 3 has an amplitude of 1 milliamp (ma) and a pulse width of 20 microseconds (μsec) for illustrative purposes only. It will be recognized that any of the characteristics of the stimulation pulse 130, including, but not limited to, the pulse shape, amplitude, pulse width, frequency, burst pattern (e.g., burst on time and burst off time), duty cycle or burst repeat interval, ramp on time, and ramp off time may vary as best serves a particular application. Moreover, the characteristics of the stimulation pulse 130 may be defined by the signal processor 105 as best serves a particular application.

The biphasic stimulation pulse 130 shown in FIG. 3 is "charge balanced" because the negative area A1 is equal to the positive area A2. A charge-balanced biphasic pulse is often employed as the stimulus to minimize electrode corrosion and charge build-up which can harm surrounding tissue. However, it will be recognized that the biphasic stimulation pulse 130 may alternatively be charge-imbalanced as best serves a particular application.

As mentioned, it is often undesirable to apply stimulation current via all M stimulation channels to the cochlea of a patient at once or during a single stimulation frame. For example, if an incoming audio signal contains human speech in the presence of a lot of background noise, the patient may not be able to distinguish the human speech from the background noise if stimulation current is applied via all M stimulation at once.

Hence, in some examples, a stimulation strategy known as an "N-of-M" strategy is used. In an N-of-M strategy, stimulation current is only applied via N of the M stimulation channels during each stimulation frame, where N is less than M. For example, in some N-of-M strategies, the cochlear implant system 100 is configured to apply stimulation current via a number of stimulation channels corresponding to the N "most relevant" stimulation channels. The N "most relevant" stimulation channels may refer to the N stimulation channels with the highest detected energy signals within the M stimulation channels. To illustrate, if there are 8 stimulation channels (e.g., M is equal to 8 and N is equal to 4, an exemplary N-of-M stimulation strategy selects the 4 highest energy-containing stimulation channels through which stimulation current is applied during a particular stimulation frame.

However, N-of-M strategies result in portions of an incoming audio signal being left out when the audio signal is presented to a patient in the form of electrical stimulation via the N stimulation channels. For example, if only 4 stimulation channels are selected out of 8 possible stimulation channels (i.e., N is equal to 4 and M is equal to 8, some information within the audio signal is lost when presented to the patient. The lost information may sometimes include relevant information (e.g., speech) in the presence of irrelevant information (e.g., background noise). As used herein, the term "relevant information" will be used to refer to speech, music, or any other audio signal of relevance to a patient. The term "irrelevant information" will be used herein to refer to portions of an audio signal that are not of relevance to a patient such as, but not limited to, background noise.

Figure 4:
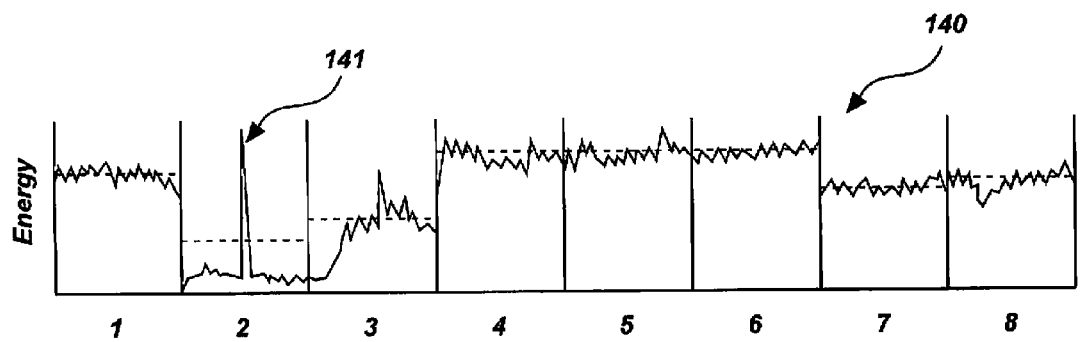
FIG. 4 illustrates an exemplary audio signal in the frequency domain that may be presented to a patient during a stimulation frame with a cochlear implant system according to principles described herein.

An example will now be given in connection with FIG. 4 that illustrates how relevant information within an audio signal may be lost while using an N-of-M stimulation strategy. FIG. 4 illustrates an exemplary audio signal 140 in the frequency domain that may be presented to a patient during a stimulation frame with a cochlear implant system 100. As shown in FIG. 4, the audio signal 140 may be divided into eight analysis channels. However, it will be recognized that the audio signal 140 may be divided into any number of analysis channels as best serves a particular application. In some examples, each analysis channel shown in FIG. 4 is mapped to one of the stimulation channels 129 shown in FIG. 2.

The vertical axis in FIG. 4 represents the amount of signal energy within each analysis channel. As shown in FIG. 4, each analysis channel contains varying energy levels. In some examples, the energy detection stages 126 within the signal processor 105 are configured to average the total amount of energy contained within each analysis channel. The horizontal dashed lines represent the average energy level contained within each analysis channel. An N-of-M stimulation strategy may then be used to select a number of analysis channels 124 for presentation to a patient that correspond to the N analysis channels that contain the highest average energy levels.

For example, if N is equal to 4, an exemplary N-of-M stimulation strategy may be used to select the four analysis channels with the highest average energy levels for presentation to a patient. In the example of FIG. 4, the four analysis channels with the highest average energy levels are channels 1, 4, 5, and 6.

In some instances, as described previously, relevant information may be included in one of the analysis channels that is not selected for presentation to a patient. For example, channel 2 includes a narrow peak 141 that may represent relevant information such as, but not limited to, human speech. However, because the energy detection stages 126 average the total amount of energy contained within each analysis channel, the average energy level of channel 2 may be lower than the average energy levels of the other channels (e.g., channels 1, 4, 5, and 6. Hence, an N-of-M stimulation strategy that selects channels 1, 4, 5, and 6 would result in the relevant information represented by the peak 141 being lost.

Hence, the systems and methods described herein may be used to prevent relevant information from being lost when an audio signal is presented to a patient in the form of electrical stimulation. To this end, as will be described in more detail below, the signal processor 105 includes more analysis channels 124 than there are stimulation channels 129. For example, if the ICS 107 includes M stimulation channels 129, the signal processor 105 may include x*M analysis channels 124, where x is an integer greater than zero and where the symbol "*" represents multiplication. However, it will be recognized that the signal processor 105 may include any number of analysis channels 124 that is greater than the number of stimulation channels 129.

Figure 5:
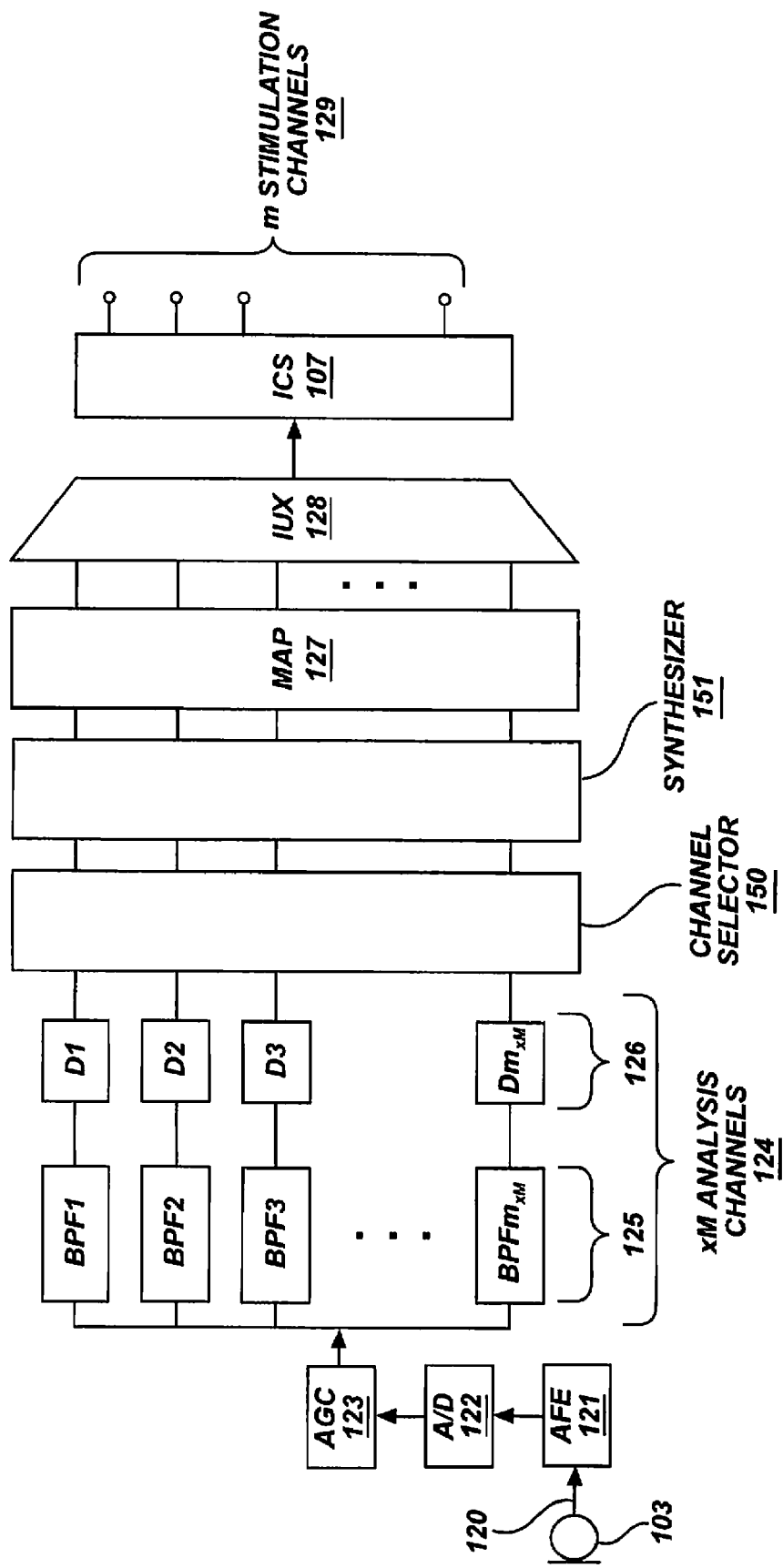
FIG. 5 illustrates an exemplary signal processor wherein the number of analysis channels contained therein is greater than the number of stimulation channels according to principles described herein.

FIG. 5 illustrates an exemplary signal processor 105 wherein the number of analysis channels 124 contained therein is greater than the number of stimulation channels 129. As shown in FIG. 5, M stimulation channels 129 are coupled to the ICS 107 and x*M analysis channels 124 are included within the signal processor 105. As will be described in more detail below, each of the M stimulation channels 129 may correspond to any number of analysis channels 124. For example, if x is equal to four, each stimulation channel 129 may correspond to four analysis channels 124.

As shown in FIG. 5, each analysis channel 124 includes a band-pass filter 125 and a corresponding energy detection stage 126. Because there are more analysis channels 124 than there are stimulation channels 129, the bandwidth of each of the analysis channels 124 is smaller than the bandwidth of each of the stimulation channels 129. For example, if the signal processor 105 includes four analysis channels 124 for every stimulation channel 129, each analysis channel 124 has a bandwidth that is one-fourth the bandwidth of each stimulation channel 129. In this manner, as will be described in more detail below, the likelihood that relevant information within an audio signal will be detected and presented to a patient is increased.

In some alternative examples, the signal processor 105 may be configured to apply a masking function to the audio signal prior to detecting the energy level within each analysis channel 124. The masking function may be configured to filter the audio signal and remove portions thereof that are not audible to normal listeners. A variety of techniques may be used to perform the masking function as may serve a particular application.

After the energy level within each analysis channel 124 is detected, a channel selector stage 150 may be configured to select one or more analysis channels 124 for presentation to the patient. In other words, information contained within the one or more analysis channels 124 that are selected by the channel selection stage 150 is used to define stimulation current that is applied to the patient via one or more of the stimulation channels 129 during a stimulation frame.

The channel selector stage 150 may include any combination of hardware, software, and/or firmware as best serves a particular application. Moreover, the manner in which the channel selector stage 150 selects the one or more analysis stimulation channels 124 may vary as best serves a particular application. For example, the channel selector stage 150 may select one or more of the analysis channels 124 that have the highest energy levels as detected by the energy detection stages 126. Alternatively, the channel selector stage 150 may use a psychophysical model, such as one utilized in MP3 audio compression, to select the most relevant analysis channels 124. In some examples, the channel selector stage 150 sets the energy level of the unselected analysis channels 124 to zero.

The number of analysis channels 124 selected by the channel selector stage 150 may vary as best serves the particular stimulation strategy being used. For example, in some stimulation strategies, the channel selector stage 150 is configured to select approximately one-half of the analysis channels 124 for presentation to the patient. However, the ratio of selected to unselected analysis channels 124 may be any number as best serves the particular stimulation strategy being used. Moreover, the number of selected analysis channels 124 may vary from one stimulation frame to another.

Once one or more of the analysis channels 124 are selected by the channel selector stage 150, the signals within each of the analysis channels 124 are input into a synthesizer stage 151. The synthesizer stage 151 is configured to combine the selected analysis channels 124 that correspond to each stimulation channel 129 so that the information contained within the selected analysis channels 124 may be mapped to corresponding stimulation channels 129. The selected analysis channels 124 may be combined using any method as best serves a particular application. For example, the synthesizer stage 151 may be configured to sum the energy levels within each group of selected analysis channels 124 that corresponds to a particular stimulation channel 129. For example, if two selected analysis channels 124 correspond to a particular stimulation channel 129, the synthesizer stage 151 may be configured to sum the energy levels of the two selected analysis channels 124.

Once the selected analysis channels 124 corresponding to each stimulation channel 129 are synthesized, the synthesized analysis channels 124 may be mapped to corresponding stimulation channels 129.

An exemplary stimulation strategy wherein the number of analysis channels is greater than the number of stimulation channels will now be described in connection with FIG. 6. In particular, FIG. 6 is a graphical illustration of a process of selecting, synthesizing, and mapping a number of analysis channels 124 to corresponding stimulation channels 129.

Figure 6:
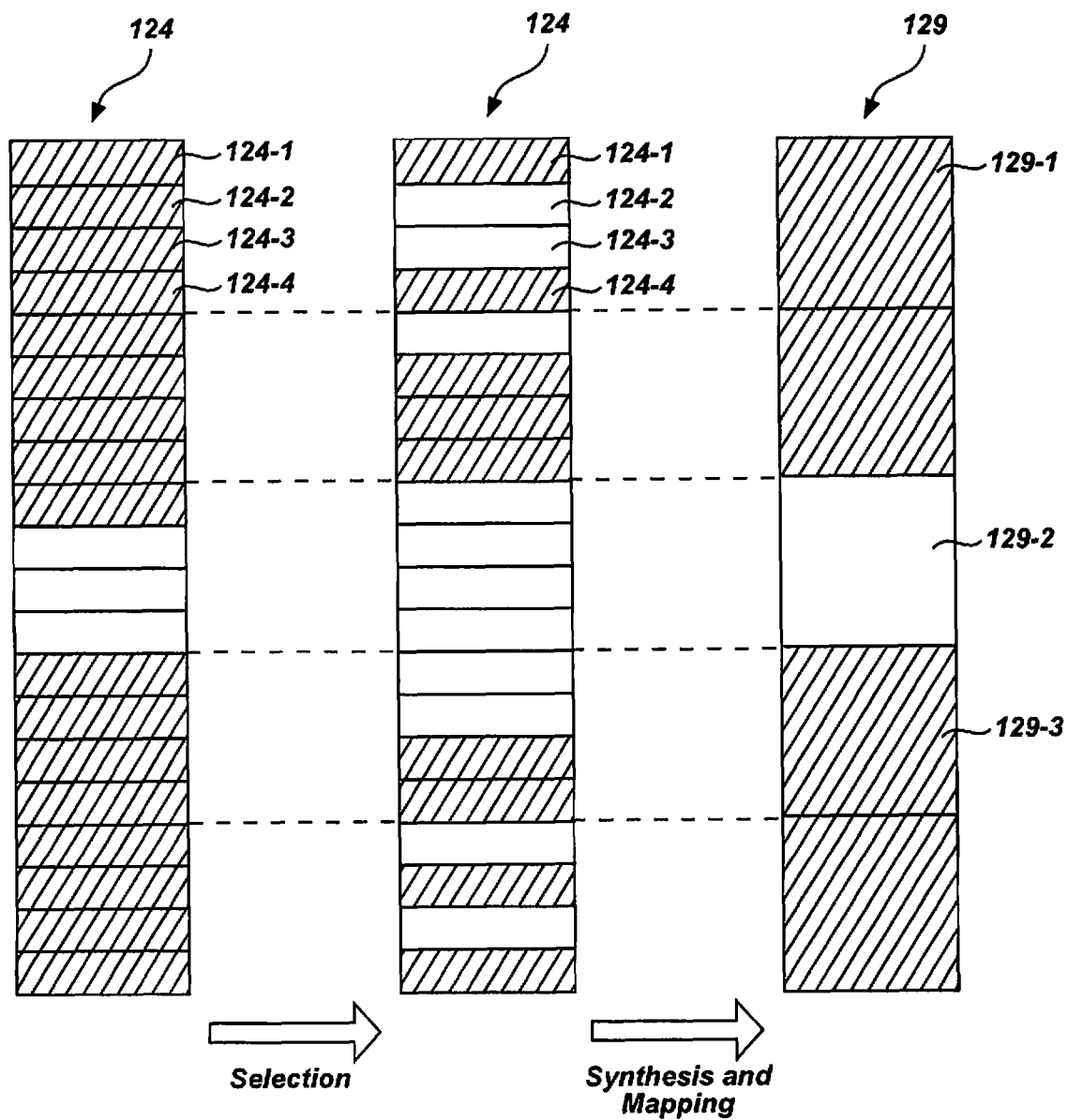
FIG. 6 is a graphical illustration of a process of selecting, synthesizing, and mapping a number of analysis channels to corresponding stimulation channels according to principles described herein.

The first or left-most column of blocks shown in FIG. 6 represents a number of analysis channels 124. Each block within the first column represents a particular analysis channel 124. As shown in FIG. 6, a number of the analysis channels 124 are represented with a hatch pattern to indicate that they contain a particular energy level. It will be recognized that the energy level may be different for each of the analysis channels 124.

In addition, a number of the analysis channels 124 within the first column may not have any energy level associated therewith. Such analysis channels 124 are represented by blocks not having the hatch pattern. For example, FIG. 6 shows three analysis channels 124 in the first column that do not have any energy level associated therewith.

As described previously in connection with FIG. 5, a channel selector stage 150 may be configured to select one or more of the analysis channels 124 shown in the first column for presentation to a patient. In other words, information contained within the one or more analysis channels 124 that are selected by the channel selection stage 150 is used to define stimulation current that is applied to the patient via one or more of the stimulation channels 129 during a stimulation frame.

Hence, the second or middle column of blocks shown in FIG. 6 shows which of the analysis channels 124 have been selected by the channel selector stage 150. The selected analysis channels 124 are represented by blocks with hatch patterns within the second column. For example, as shown in FIG. 6, nine out of twenty analysis channels 124 have been selected by the channel selection stage 150. It will be recognized that any number of analysis channels 124 may be selected for presentation to a patient.

The manner in which the channel selector stage 150 selects the one or more analysis stimulation channels 124 may vary as best serves a particular application. For example, the channel selector stage 150 may select one or more of the analysis channels 124 that have the highest energy levels.

In some examples, the energy levels of the unselected analysis channels 124 are set to zero. In this manner, the unselected analysis channels 124 may be included within the synthesis process. In other words, the unselected analysis channels 124 may be included within an averaging algorithm used in the synthesis process. Alternatively, the unselected analysis channels 124 may be ignored during the synthesis process.

Once one or more of the analysis channels 124 have been selected for presentation to a patient, the selected analysis channels 124 may be synthesized and mapped to corresponding stimulation channels 129. The third or right-most column of blocks shown in FIG. 6 represents a number of stimulation channels 129. As shown in FIG. 6, each stimulation channel 129 corresponds to a number of analysis channels 124. For example, each stimulation channel 129 shown in FIG. 6 corresponds to four analysis channels 124, as indicated by the horizontal dashed lines. It will be recognized that each stimulation channel 129 may correspond to any number of analysis channels 124 as best serves a particular application. Moreover, it will be recognized that a particular stimulation channel 129 may correspond to a different number of analysis channels 124 than another stimulation channel 129. For example, a first stimulation channel may correspond to four analysis channels 124 and a second stimulation channel may correspond to one analysis channel 124. However, it will be assumed that each stimulation channel 129 corresponds to four analysis channels 124 in the examples given herein for illustrative purposes.

The selected analysis channels 124 may be synthesized using any suitable method as best serves a particular application. In some examples, the energy levels within each group of selected analysis channels 124 that corresponds to a particular stimulation channel 129 are summed and/or averaged. For example, if analysis channels labeled 124-1 through 124-4 correspond to the stimulation channel labeled 129-1, synthesis may be performed by summing the energy levels of the selected analysis channels 124-1 and 124-4.

In some examples, as previously mentioned, the energy levels of the unselected analysis channels 124-2 and 124-3 may be set to zero. In this manner, the synthesizer stage 151 may also include the unselected analysis channels (e.g., 124-2 and 124-3 in the summing function.

In some examples, none of the analysis channels 124 corresponding to a particular stimulation channel 129 are selected for presentation to a patient. For example, none of the analysis channels 124 corresponding to the stimulation channel labeled 129-2 shown in FIG. 6 have been selected for presentation to a patient. In some examples, the time frame dedicated to the stimulation channel 129-2 may be used to present information for the next stimulation channel 129 that contains relevant energy (e.g., the stimulation channel labeled 129-3. By so doing, the net stimulation rate may be increased, which may be beneficial for some patients.

Once the selected analysis channels 124 corresponding to each stimulation channel 129 are synthesized, the synthesized analysis channels 124 may be mapped to corresponding stimulation channels 129. By dividing the audio signal into more analysis channels 124 than there are stimulation channels 129, the likelihood that relevant information within the audio signal will be included within the information that is selected for presentation to the patient increases. To illustrate, the audio signal 140 of FIG. 4 is shown again in FIG. 7. However, as shown in FIG. 7, the audio signal 140 is divided into 32 analysis channels instead of into 8 analysis channels as shown in FIG. 4.

Figure 7:
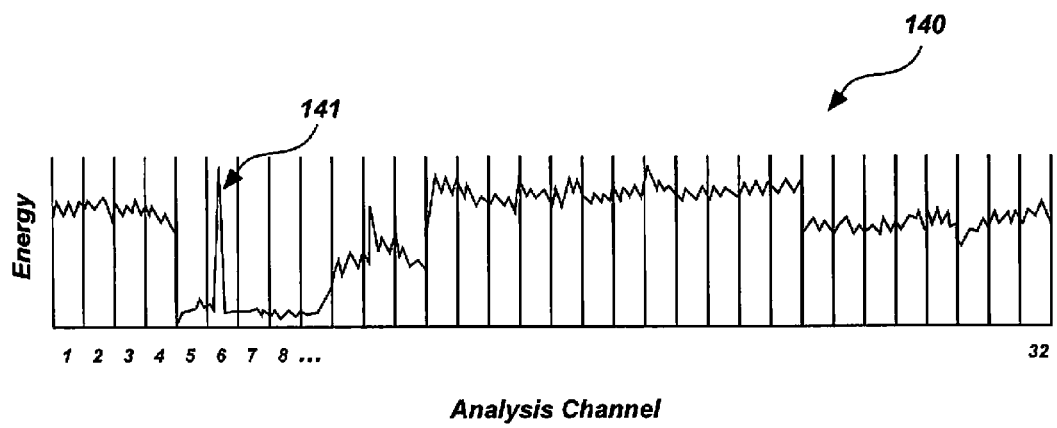
FIG. 7 illustrates the exemplary audio signal of FIG. 4 divided into 32 analysis channels according to principles described herein.

Because the audio signal 140 is divided into 32 analysis channels, each analysis channel shown in FIG. 7 is more narrow in bandwidth than each analysis channel shown in FIG. 4. Hence, a stimulation strategy that selects the highest average energy-containing channels shown in FIG. 7 for presentation to a patient will select channel 6, which contains the narrow peak 141.

Figure 8:
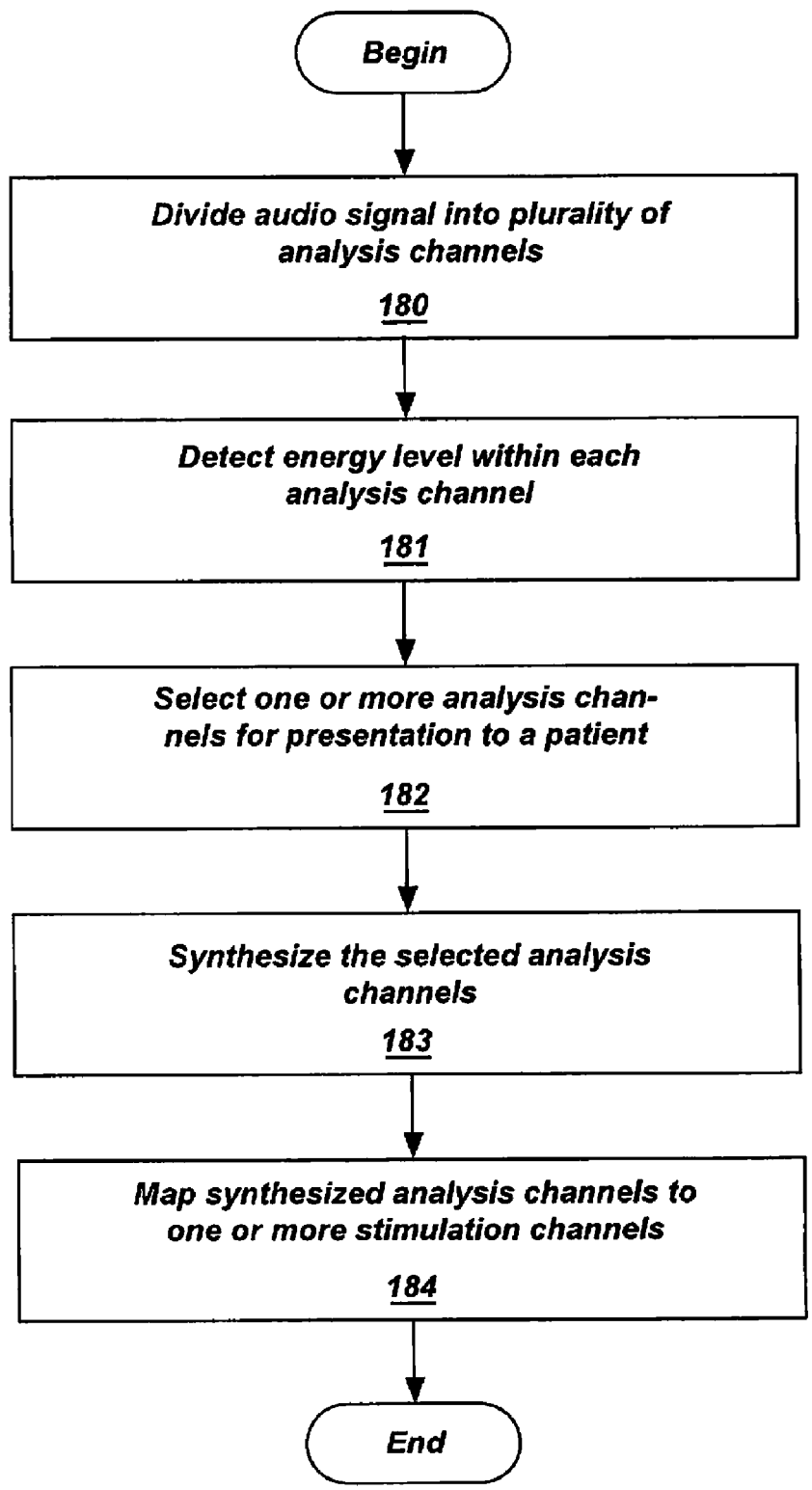
FIG. 8 is a flow chart illustrating an exemplary method of presenting an audio signal to a patient with a cochlear implant system according to principles described herein.

FIG. 8 is a flow chart illustrating an exemplary method of presenting an audio signal to a patient with a cochlear implant system. The steps shown in FIG. 8 are merely exemplary and may be omitted, added to, reordered, and/or modified.

In step 180, an audio signal is divided into a plurality of analysis channels 124. In some examples, as described previously, a number of band-pass filters may be used to divide the audio signal into the analysis channels 124. The total number of analysis channels 124 is greater than the total number of stimulation channels 129 that are coupled to or a part of the ICS 107.

In step 181, the energy level of the audio signal within each analysis channel 124 is detected. One or more energy detection stages 126 may be configured to detect the energy levels within each of the analysis channels 124. In some examples, the energy detection stages 126 are configured to calculate an average energy level within each analysis channel 124.

In some alternative examples, a masking function may be applied to the audio signal prior to step 181. The masking function may be configured to filter the audio signal and remove portions thereof that are not audible to normal listeners. A variety of techniques may be used to perform the masking function as may serve a particular application.

Once the energy level of the audio signal within each analysis channel 124 is detected, one or more of the analysis channels 124 may then be selected for presentation to the patient, as shown in step 182. The particular method used to select the analysis channels 124 may vary as best serves a particular application. For example, one or more of the analysis channels 124 having the highest average energy levels may be selected for presentation to the patient.

The selected analysis channels 124 may then be synthesized, as shown in step 183. In some examples, a synthesizer stage 151 is configured to synthesize the selected analysis channels 124 by summing the detected energy levels within each group of selected analysis channels 124 that corresponds to each stimulation channel 129.

In step 184, the synthesized analysis channels are mapped to one or more stimulation channels 129. Stimulation current representative of the audio signal may then be applied via one or more of the stimulation channels 129 to one or more stimulation sites within the cochlea of the patient.

The preceding description has been presented only to illustrate and describe embodiments of the invention. It is not intended to be exhaustive or to limit the invention to any precise form disclosed. Many modifications and variations are possible in light of the above teachings.

What is claimed is:

1. A signal processing unit comprising:
a plurality of filters configured to divide an audio signal into a plurality of analysis channels;

one or more detection stages configured to detect an energy level within each of said analysis channels;

a selection stage configured to select one or more of said analysis channels for presentation to a patient;

a synthesizer stage configured to synthesize said selected analysis channels; and a mapping stage configured to map said selected analysis channels to a number of stimulation channels within an implantable cochlear stimulator;

wherein a total number of said analysis channels is greater than a total number of said stimulation channels.

2. The signal processing unit of claim 1, wherein information within each of said synthesized analysis channels defines one or more stimulation current pulses delivered to a cochlea of patient via said one or more stimulation channels during a stimulation frame.

3. The signal processing unit of claim 1, wherein each of said stimulation channels corresponds to a group of one or more of said analysis channels.

4. The signal processing unit of claim 3, wherein said synthesizer stage is further configured to synthesize said selected analysis channels by summing said energy levels of each of said selected analysis channels within each of said groups of said analysis channels.

5. The signal processing unit of claim 1, wherein said plurality of said analysis channels comprises one or more analysis channels that are not selected for presentation to said patient, wherein said energy levels of said selected analysis channels are greater than said energy levels of said unselected analysis channels.

6. A signal processing unit comprising:

one or more detection stages configured to detect an energy level within each of a plurality of analysis channels corresponding to a single stimulation channel;

a selection stage configured to select a subset of the analysis channels for presentation to a patient based on the detected energy levels;

a synthesizer stage configured to synthesize the selected subset of analysis channels; and a mapping stage configured to map the synthesized subset of analysis channels to the single stimulation channel.

7. The signal processing unit of claim 6, wherein the signal processing unit is configured to direct an implantable cochlear stimulator to apply a stimulation current to the patient via the single stimulation channel in accordance with information contained within the synthesized subset of analysis channels.

8. The signal processing unit of claim 6, wherein the synthesizer stage is configured to synthesize the selected subset of analysis channels by summing the detected energy levels of each of the analysis channels included in the selected subset of analysis channels.

9. The signal processing unit of claim 6, wherein the synthesizer stage is configured to synthesize the selected subset of analysis channels by averaging the detected energy levels of each of the analysis channels included in the selected subset of analysis channels.

10. The signal processing unit of claim 6, wherein:

the one or more detection stages are further configured to detect an energy level within each of an additional plurality of analysis channels corresponding to an additional single stimulation channel;

the selection stage is further configured to select an additional subset of the additional analysis channels for presentation to the patient based on the detected energy levels of the additional analysis channels;

the synthesizer stage is further configured to synthesize the selected additional subset of analysis channels; and the mapping stage is further configured to map the synthesized additional subset of analysis channels to the additional single stimulation channel.

11. The signal processing unit of claim 10, wherein the signal processing unit is configured to direct an implantable cochlear stimulator to apply a stimulation current to the patient via the additional single stimulation channel in accordance with information contained within the synthesized additional subset of analysis channels.

* * * * *